(12) United States Patent
Croft et al.

(10) Patent No.: US 9,588,062 B2
(45) Date of Patent: Mar. 7, 2017

(54) WASTE WATER ASSESSMENT (71) Applicant: DES19N Limited, Loughborough, Leicestershire (GB)

(72) Inventors: Martin James Croft, Leicestershire (GB); Duncan Kenneth Wallace, Nottingham (GB)

(73) Assignee: DES19N Limited, Loughborough, Leicestershire (GB)

( * ) Notice: Subject to any disclaimer, the term of this patent is extended or adjusted under 35 U.S.C. 154(b) by 0 days.

(21) Appl. No.: 15/150,088

(22) Filed: May 9, 2016

(65) Prior Publication Data

US 2016/0252466 A1   Sep. 1, 2016

Related U.S. Application Data

(63) Continuation of application No. 13/634,195, filed as application No. PCT/GB2011/050437 on Mar. 7, 2011, now Pat. No. 9,341,581.

(51) Int. Cl.
*G01N 23/02* (2006.01)
*G01F 1/00* (2006.01)
(Continued)

(52) U.S. Cl.
CPC ............ *G01N 22/02* (2013.01); *G01F 1/002* (2013.01); *G01F 1/52* (2013.01); *G01F 1/56* (2013.01);
(Continued)

(58) Field of Classification Search
CPC ... G01F 1/00; G01F 1/66; G01F 1/663; G01F 23/284; G01N 22/00; G01S 7/02;
(Continued)

(56) References Cited

U.S. PATENT DOCUMENTS 3,357,014 A   12/1967 Atlas
3,954,009 A   5/1976 Lederer
(Continued)

FOREIGN PATENT DOCUMENTS

DE   3223393 A1   12/1983
EP   0681683 B1   11/1995
(Continued)

OTHER PUBLICATIONS

Carrondo, M.J.T., et al., "Analysis of Heavy Metals in Sewage Sludge, Sewages and Final Effluent," Public Heath and Water Resource Engineering Section, Civil Engineering Department, Imperial College, London, Nov. 1978, 122 pages.
(Continued)

*Primary Examiner* — Laura Martin
*Assistant Examiner* — Irving A Campbell
(74) *Attorney, Agent, or Firm* — Conley Rose, P.C.; J. Robert Brown, Jr.

(57) ABSTRACT

Waste water assessment apparatus, a method and a computer program are provided. The waste water assessment apparatus comprises: transceiver circuitry configured to transmit a microwave signal and to receive one or more reflections of the microwave signal; and processing circuitry configured to process the one or more reflections of the microwave signal to determine one or more characteristics of waste water flowing through a conduit.

20 Claims, 5 Drawing Sheets

(51) Int. Cl.

| | | |
|---|---|---|
| G01F 1/52 | (2006.01) | |
| G01F 1/56 | (2006.01) | |
| G01F 23/284 | (2006.01) | |
| G01N 22/00 | (2006.01) | |
| G01N 33/18 | (2006.01) | |
| G01S 13/02 | (2006.01) | |
| G01S 13/88 | (2006.01) | |
| G08B 3/10 | (2006.01) | |
| G08B 5/22 | (2006.01) | |
| G08B 21/12 | (2006.01) | |
| G08B 21/18 | (2006.01) | |
| G01N 22/02 | (2006.01) | |
| G01S 7/41 | (2006.01) | |

(52) U.S. Cl.
CPC .......... *G01F 23/284* (2013.01); *G01N 22/00* (2013.01); *G01N 33/18* (2013.01); *G01S 13/0209* (2013.01); *G01S 13/88* (2013.01); *G08B 3/10* (2013.01); *G08B 5/22* (2013.01); *G08B 21/12* (2013.01); *G08B 21/182* (2013.01); *G01S 7/411* (2013.01)

(58) Field of Classification Search
CPC .......... G01S 13/00; G01S 13/02; G01S 13/08; G01S 13/50; G01S 13/505; G01S 13/524; E03F 2201/40
USPC .... 73/53.01, 290 R, 290 B, 290 V, 291–334, 73/861.04, 861.25–861.31, 861.42, 73/861.49, 862.51; 116/276; 340/607, 340/608, 612; 342/124
See application file for complete search history.

(56) References Cited

U.S. PATENT DOCUMENTS

| | | | |
|---|---|---|---|
| 4,546,346 | A | 10/1985 | Wave et al. |
| 5,049,823 | A | 9/1991 | Castel et al. |
| 5,550,537 | A | 8/1996 | Perdue |
| 5,614,911 | A | 3/1997 | Otto et al. |
| 5,793,216 | A | 8/1998 | Constant |
| 5,811,688 | A | 9/1998 | Marsh et al. |
| 5,969,666 | A | 10/1999 | Burger et al. |
| 6,843,124 | B2 | 1/2005 | Otto et al. |
| 6,987,393 | B2 | 1/2006 | Jean et al. |
| 9,341,581 | B2 | 5/2016 | Croft et al. |
| 2004/0229376 | A1 | 11/2004 | Beauducel et al. |
| 2007/0297741 | A1 | 12/2007 | Linder |
| 2008/0098817 | A1 | 5/2008 | Jones |
| 2009/0032304 | A1 | 2/2009 | Groh |
| 2009/0278730 | A1 | 11/2009 | Taylor |
| 2011/0301877 | A1 | 12/2011 | Wee et al. |

FOREIGN PATENT DOCUMENTS

| | | |
|---|---|---|
| EP | 0953827 B1 | 11/1999 |
| EP | 1428033 | 6/2004 |
| JP | 60100017 A | 6/1985 |
| JP | 2002139456 A | 5/2002 |
| JP | 2005241343 A | 9/2005 |
| JP | 200717454 A | 1/2007 |
| WO | 9515481 A1 | 6/1995 |
| WO | 03019207 A1 | 3/2003 |
| WO | 2008077041 A2 | 6/2008 |
| WO | 2011110835 A2 | 9/2011 |

OTHER PUBLICATIONS

Godley, Andrew, Elsevier, "Flow Measurement in Partially Filled Closed Conduits," www.elsevier.com/locate/flowmeasinst, 2002, 5 pages.

Keating, Kay, "Toiletology 101," http://web.archive.org/web/20060615084655/http://www.toiletology.com/emergenc.shtml, archived Jun. 15, 2006, 5 pages.

Kraszewski, Andrzej W., "Microwave Aquametry—Needs and Perspectives, IEEE Transactions on Microwave Theory and Techniques," vol. 39. No. 5, May 1991, 8 pages.

Li, Hsueh-Jyn, et al., The Electrical Engineering Handbook, "Radar and Inverse Scattering," Jan. 1, 2005, 10 pages.

Morris, Alan S., "ISO 14000 Environmental Management Standards, Engineering and Financial Aspects," Department of Automatic Control and Systems Engineering, 6 pages.

Hmart Vega, "Level Measurement Radar," Vegapuls 61, Vegapuls 62, Vegapuls 63, Vegapuls 65, Vegapuls 66, Product Information, 38 pages.

Patrcevic, Vladimir, et al., "Sewer Flow Monitoring," International Symposium on Water Management and Hydraulic Engineering, Sep. 1-5, 2009, 14 pages.

Samhan, Omar, et al., "Trace Metals and Chlorinated Hydrocarbons in Sewage Sludges of Kuwait," Water, Air, and Soil Pollution, 1987, 36, pp. 239-246.

Office Action dated Jan. 31, 2014; U.S. Appl. 13/634,195, filed Sep. 11, 2012; 27 pages.

Final Office Action dated Jul. 29, 2014; U.S. Appl. 13/634,195, filed Sep. 11, 2012; 16 pages.

Office Action dated Dec. 17, 2014; U.S Appl. 13/634,195, filed Sep. 11, 2012; 30 pages.

Final Office Action dated Jul. 7, 2015; U.S. Appl. 13/634,195, filed Sep. 11, 2012; 29 pages.

Advisory Action dated Oct. 19, 2015; U.S. Appl. 13/634,195, filed Sep. 11, 2012; 3 pages.

Notice of Allowance dated Jan. 14, 2016; U.S. Appl. 13/634,195, filed Sep. 11, 2012; 8 pages.

PCT International Search Report; PCT Application No. PCT/GB2011/050437; Jan. 16, 2012; 8 pgs.

PCT Written Opinion of the International Searching Authority; PCT Application No. PCT/GB2011/050437; Jan. 16, 2012; 9 pgs.

GB Search Report; GB Application No. GB1004139.0; dated Aug. 19, 2010; 1 page.

GB Examination Report; GB Application No. GB1004139.0; dated Jul. 4, 2013; 5 pages.

WASTE WATER ASSESSMENT

CROSS-REFERENCE TO RELATED APPLICATIONS

This application is a continuation of U.S. patent application Ser. No. 13/634,195 filed Sep. 11, 2012 entitled "Waste Water Assessment", claiming priority to 35 U.S.C. 371 of International Application No. PCT/GB2011/050437 filed Mar. 7, 2011, entitled "Waste Water Assessment" claiming priority to GB Application No. 1004139.0 filed on Mar. 12, 2010, entitled "Waste Water Assessment", which are incorporated by reference herein as if reproduced in their entirety.

FIELD

Embodiments of the present invention relate to waste water assessment. In particular, they relate to assessing waste water using microwave signals.

BACKGROUND

Private and commercial properties include waste water drainage systems for draining waste water into public sewers. The water bill received by an owner or a tenant of a property may be estimated. The estimation may depend upon the amount of water that is used by the property and the surface area of land associated with the property, rather than an accurate assessment of the amount of water that is drained away from the property.

Waste water from some properties may include more impurities than waste water from others. Waste water from some properties may include illegal discharge such as suspended metals (for example, chrome, zinc or copper) and paint. At present, many water companies are unable to assess which properties these are and consequently, the water companies are unable to take appropriate action.

BRIEF DESCRIPTION OF VARIOUS EMBODIMENTS OF THE INVENTION

According to various, but not necessarily all, embodiments of the invention there is provided waste water assessment apparatus, comprising: transceiver circuitry configured to transmit a microwave signal and to receive one or more reflections of the microwave signal; and processing circuitry configured to process the one or more reflections of the microwave signal to determine one or more characteristics of waste water flowing through a conduit.

The processing circuitry may be configured to process the one or more reflections of the microwave signal to determine the amount of waste water flowing through the conduit. The processing circuitry may be configured to determine the amount of waste water flowing through the conduit at a particular time by determining a distance between the transceiver circuitry and a surface of the waste water flowing through the conduit. The at least one property may be the amplitude of the first reflection of the microwave signal relative to the amplitude of the transmitted microwave signal.

The processing circuitry may be configured to determine the amount of waste water flowing through the conduit at a particular time by processing at least one property of a first reflection of the microwave signal. The processing circuitry may be configured to determine the amount of waste water that has flowed through the conduit over a period of time by processing at least one property of a first reflection of the microwave signal. The at least one property may be the time elapsed between the transmission of the microwave signal and the reception of the first reflection of the microwave signal.

The transceiver circuitry may be configured to transmit a microwave signal periodically over a period of time. The processing circuitry may be configured to process reflections of the periodically transmitted microwave signals to estimate the quantity of water that has flowed through the conduit over the period of time.

The processing circuitry may be configured to process the one or more reflections of the microwave signal to determine whether one or more impurities are present in the waste water.

The one or more impurities may comprise one or more hydrocarbons and/or one or more metals. The processing circuitry may be configured to determine whether one or more impurities are present in the waste water by determining at least one of: an amplitude, phase, frequency, polarization and degree of scattering of one or more reflections of the microwave signal.

The processing circuitry may be configured to process the one or more reflections of the microwave signal to determine the quantity of a particular impurity present in the waste water.

The transmitted microwave signal may be an ultra wide band microwave signal.

The waste water apparatus may further comprise a waveguide configured to guide transmitted microwave signals through a wall of the conduit.

According to various, but not necessarily all, embodiments of the invention there is provided waste water assessment apparatus, comprising: processing circuitry; and memory circuitry storing computer program instructions that, when executed by the processing circuitry, cause the processing circuitry to perform at least the following: processing one or more reflections of a microwave signal to determine one or more characteristics of waste water flowing through a conduit.

According to various, but not necessarily all, embodiments of the invention there is provided a method, comprising: transmitting a microwave signal; and processing one or more reflections of the microwave signal to determine one or more characteristics of waste water flowing through a conduit.

The method may further comprise: fitting transceiver circuitry, for transmitting the microwave signal, to a position adjacent to the conduit.

According to various, but not necessarily all, embodiments of the invention there is provided a computer program comprising computer program instructions that, when executed by processing circuitry, enable the above method to be performed.

The above computer program may be stored by computer readable storage medium. The computer readable medium may be non-transitory.

According to various, but not necessarily all, embodiments of the invention there is provided waste water assessment apparatus, comprising: transceiver circuitry configured to transmit a microwave signal and to receive one or more reflections of the microwave signal; and processing circuitry configured to process the one or more reflections of the microwave signal, in order to quantify waste water flow through a closed conduit.

According to various, but not necessarily all, embodiments of the invention there is provided waste water assessment apparatus, comprising: processing circuitry; and memory circuitry storing computer program instructions that, when executed by the processing circuitry, cause the processing circuitry to perform at least the following: processing one or more reflections of a microwave signal, in order to quantify waste water flow through a closed conduit.

According to various, but not necessarily all, embodiments of the invention there is provided a method, comprising: transmitting a microwave signal; and processing one or more reflections of the microwave signal, in order to quantify waste water flow through a closed conduit.

BRIEF DESCRIPTION OF THE DRAWINGS

For a better understanding of various examples of embodiments of the present invention reference will now be made by way of example only to the accompanying drawings in which.

DETAILED DESCRIPTION

Embodiments of the invention relate to an apparatus for assessing waste water. For example, the apparatus may be used to assess the quality and/or the quantity of waste water being drained from a property.

The Figures illustrate waste water assessment apparatus 10, comprising: transceiver circuitry 14 configured to transmit a microwave signal and to receive one or more reflections of the microwave signal; and processing circuitry 12 configured to process the one or more reflections of the microwave signal 70, 75, 80 to determine one or more characteristics of waste water flowing in a conduit 90.

Figure 1:
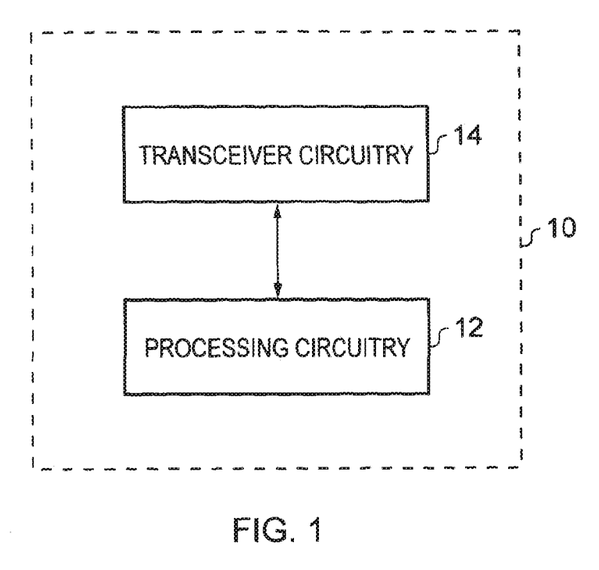
FIG. 1 illustrates a first example of waste water assessment apparatus.

FIG. 1 illustrates a first example of waste water assessment apparatus 10. The waste water assessment apparatus 10 comprises transceiver circuitry 14 and processing circuitry 12. The processing circuitry 12 is configured to provide outputs to transceiver circuitry 14 and to receive inputs from the transceiver circuitry 14. The processing circuitry 12 may consist of a single processor, or may comprise multiple processors. In some embodiments of the invention, the processing circuitry 12 is local to the transceiver circuitry 14. In other embodiments of the invention, at least some aspect of the processing circuitry 12 is remote from the transceiver circuitry 14. This will be described in further detail below.

The transceiver circuitry 14 is configured to transmit and receive microwave signals. The microwave signals may, for example, have a frequency in the range 300 MHz to 300 GHz. In particular, the microwave signals may have a frequency in the range 1 GHz to 50 GHz. The microwave signals may, for example, be Ultra Wide Band (UWB) signals.

Figure 2:
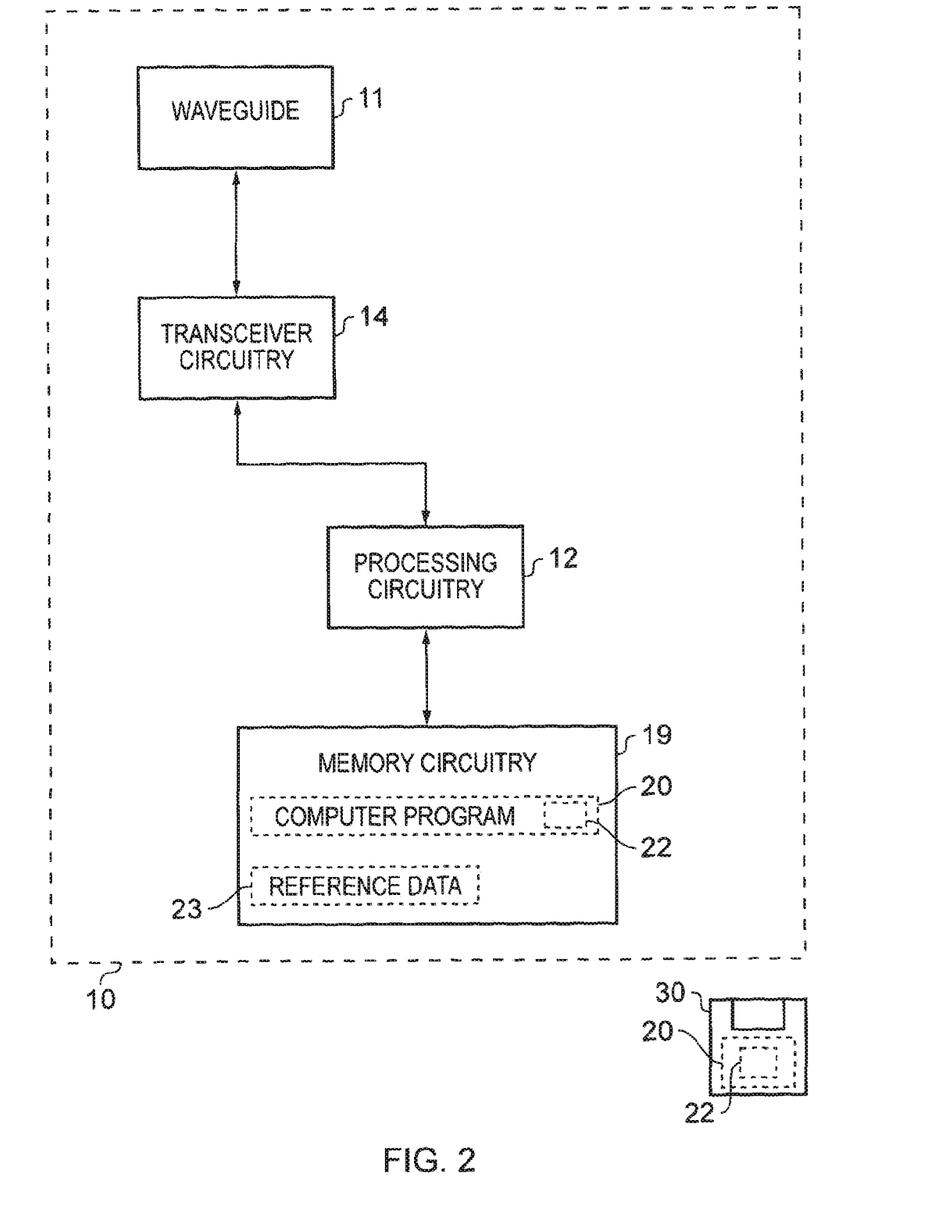
FIG. 2 illustrates a second example of waste water assessment apparatus.

FIG. 2 illustrates a second example of waste water assessment apparatus 10. The waste water assessment apparatus 10 comprises the processing circuitry 12 and the transceiver circuitry 14 described above in relation to FIG. 1.

The waste water assessment apparatus 10 illustrated in FIG. 2 further comprises a waveguide 11 and memory circuitry 19. The waveguide 11 is optional and configured to guide microwaves transmitted by the transceiver circuitry 14 in a particular direction. The waveguide 11 is also configured to guide reflected microwave signals towards the transceiver circuitry 14.

The processing circuitry 12 is configured to read from and to write to the memory circuitry 19. The memory circuitry 19 is illustrated as storing reference data 23 and a computer program 20 comprising computer program instructions 22. The reference data 23 may be a look-up table and will be described in further detail below. The computer program instructions 22 control the operation of the processing circuitry 12, when executed by the processing circuitry 12.

The computer program 20 may arrive at the apparatus 10 via any suitable delivery mechanism 30. The delivery mechanism 30 may be, for example, a non-transitory computer-readable storage medium, a computer program product, a memory device, a record medium such as a CD-ROM or DVD, or an article of manufacture that tangibly embodies the computer program 20.

Although the memory circuitry 19 is illustrated as a single component it may be implemented as one or more separate components some or all of which may be integrated/removable and/or may provide permanent/semi-permanent/dynamic/cached storage.

The elements 11, 12, 14 and 19 illustrated in FIG. 2 are operationally coupled and any number or combination of intervening elements can exist (including no intervening elements).

A method according to embodiments of the present invention will now be described in relation to FIGS. 3 to 5.

Figure 3:
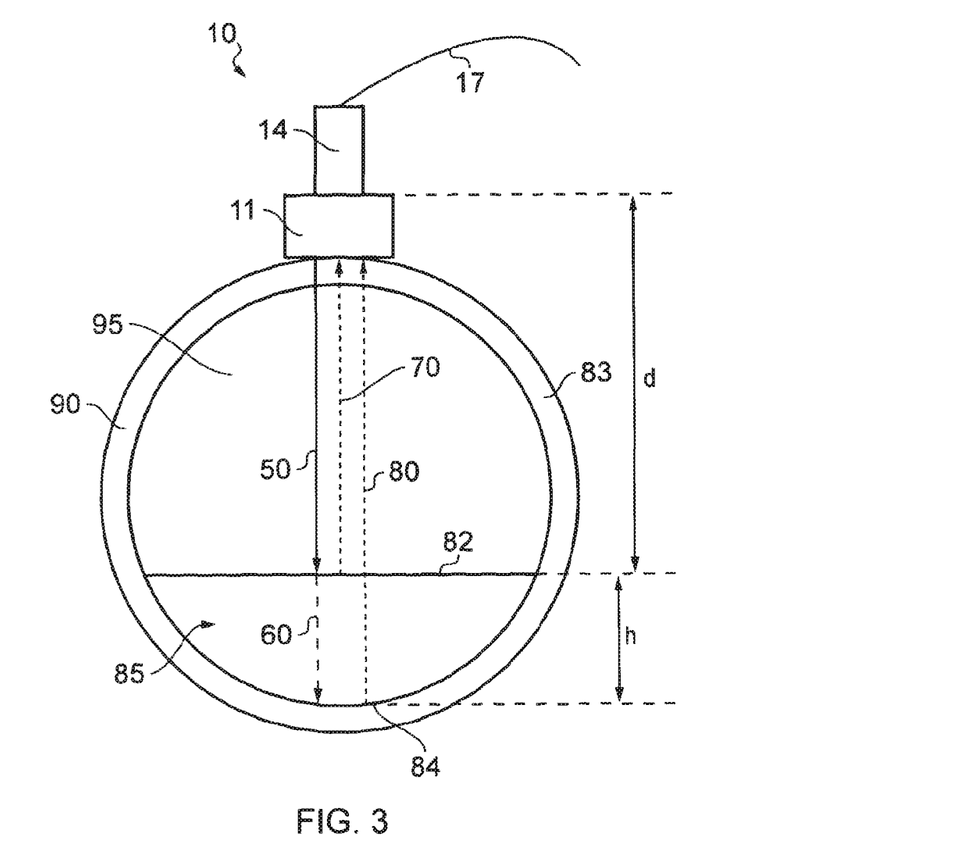
FIG. 3 illustrates the waste water assessment apparatus in operation.

FIG. 3 illustrates part of the waste water assessment apparatus 10 in operation. The transceiver circuitry 14 and the waveguide 11 are positioned adjacent a conduit 90. The waveguide 11 is situated between the transceiver circuitry 14 and an outer surface of the conduit 90. An attachment device may be provided to hold the waveguide 11 and the transceiver circuitry 14 in place adjacent the conduit 90. The transceiver circuitry 14 and the waveguide 11 may be fitted to the conduit 90 at the time a building is being built, or they may be fitted retroactively to a conduit 90 of an old building.

The conduit 90 may, for example, be a waste water pipe of a property that channels flowing waste water 85 away from the property. For example, the waste water pipe may be made from clay or a plastics material.

The shape of the conduit 90 is defined by a continuous circumferential wall 83. In this instance, the conduit 90 is considered to be 'closed' because the illustrated conduit 90 does not include an opening in its circumferential wall 83.

In this example, the conduit 90 has a circular cross section. In other examples, the cross section of the conduit 90 may be non-circular. The illustrated conduit 90 contains waste water 85 and air 95.

The waveguide 11 is configured to guide microwave signals transmitted by the transceiver circuitry 14 through the wall 83 of the conduit 90 and into the conduit 90. The waveguide 11 is also configured to guide reflections of the microwave signals travelling through the wall 83 into the transceiver circuitry 14.

In this particular example, the processing circuitry 12 and the memory circuitry 19 are remote from transceiver circuitry 14. The processing circuitry 12 is connected to transceiver circuitry 14 by a remote communication link 17. The remote communications link 17 may be wired and may be used to provide power to the transceiver circuitry 14. In this example, the remote communication link 17 comprises an optical fibre. In other examples, the remote communication link 17 may, for example, be wireless.

As mentioned above, in alternative embodiments of the invention, the processing circuitry 12 and the memory circuitry 19 may be situated adjacent to the transceiver circuitry 14. For example, the transceiver circuitry 14, the processing circuitry 12 and the memory circuitry 19 may be located in the same housing.

Figure 4:
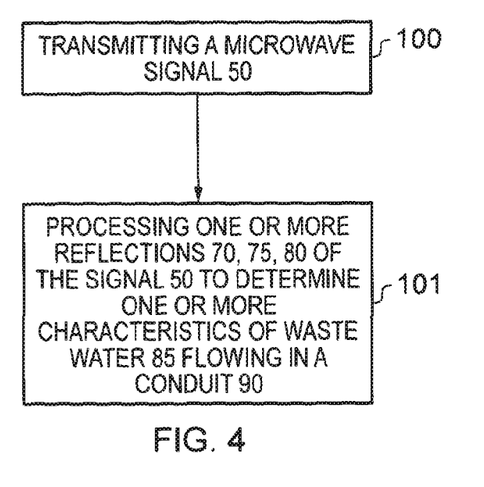
FIG. 4 illustrates a flow diagram of a method.

FIG. 4 illustrates a flow chart of a method. At block 100 of FIG. 4, the transceiver circuitry 14 transmits a microwave signal 50 at a time $t_1$. For example, the microwave signal 50 may be a UWB pulse signal spanning a wide frequency band. FIG. 3 illustrates the microwave signal 50 travelling through the wall 83 of the conduit 90.

Figure 5:
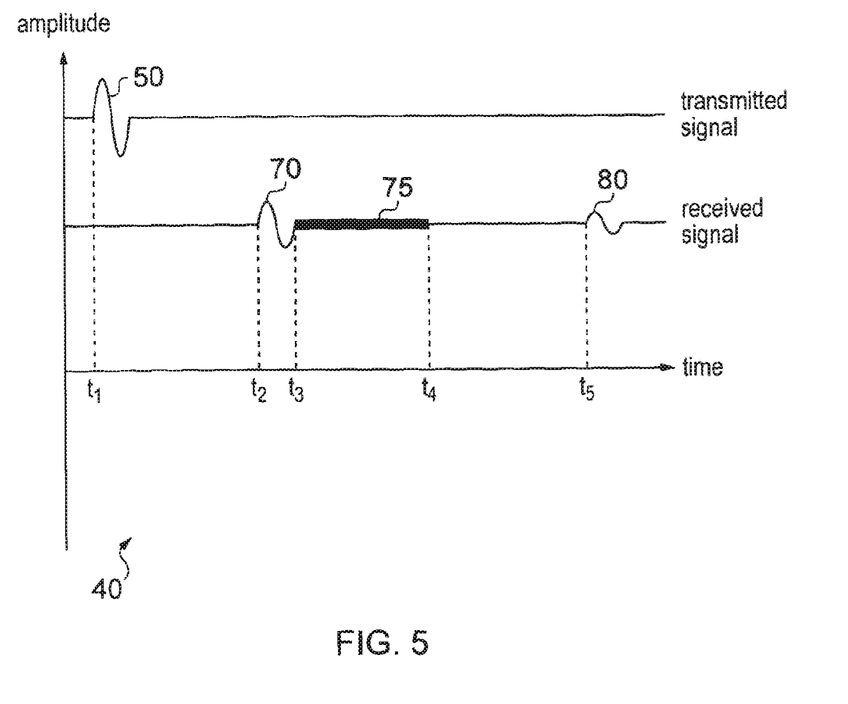
FIG. 5 illustrates a graph illustrating transmitted and received microwave signals.

FIG. 5 illustrates an amplitude-time graph 40 illustrating transmitted and received microwave signals. FIG. 5 illustrates the microwave signal 50 being transmitted at a time $t_1$.

The interaction between microwaves and their medium of propagation depends upon the permittivity of the medium. An interface between different propagation mediums will result in a microwave being strongly reflected if the contrast in the permittivity of the mediums is large.

In this example, the permittivity of the air 95 is much lower than the permittivity of the waste water 85. Thus, when the microwave signal 50 meets the surface 82 of the waste water 85, a portion of the microwave signal 50 is reflected and the remainder propagates into the waste water 85.

The dotted arrow 70 indicates a reflected portion of the microwave signal 50 travelling back towards the transceiver circuitry 14. This first reflection 70 of the microwave signal 50 is received by the transceiver circuitry 14 at a time $t_2$.

As the remaining portion of the microwave signal 50 propagates through the waste water 85, it is reflected almost continuously by the waste water 85 and the impurities contained within it. The nature of this second reflection 75 depends upon the content of the waste water 85. That is, a particular material contained in the waste water 85 may cause a reflection that to occur that has one or more properties which are characteristic of that material. For example, the second reflected signal 75 may have an amplitude, phase, frequency, polarization and/or degree of scattering that indicates that a particular material is present in the waste water 85.

The second reflected signal 75 is received over between the times indicated as $t_3$ and $t_4$ in FIG. 5. It will be appreciated by those skilled in the art the second reflected signal 75 contains very fine detail that is not shown in FIG. 5 for clarity purposes.

FIG. 3 illustrates a portion 60 of the microwave signal 50 reaching the inner surface 84 of the wall 83 of the conduit 90. When the portion 60 reaches the interface between the waste water 85 and the inner surface 84 of the wall 83, the large contrast in permittivity of the interface causes a further portion of the microwave signal 50 to be reflected. This third reflection 80 reaches the transceiver circuitry 14 at a time $t_5$. The amplitude of the third reflection 80 is typically smaller than the first reflection 70, as illustrated in FIG. 5.

It will be appreciated by those skilled in the art that further reflections of the microwave signal 50 may occur which are not illustrated in FIG. 5 for clarity purposes. For example, a further reflection may occur when the when the third reflected signal 80 crosses the interface between the waste waster 85 and the air 95.

The transceiver circuitry 14 may be configured to determine the times $t_2$, $t_3$, $t_5$ that the first, second and third reflections 70, 75, 80 are received, relative to the time at which the microwave signal 50 is transmitted. This information, along with one or more of the reflected signals 70, 75 and 80, may be provided to the processing circuitry 12 via the communication link 17.

At block 101 of FIG. 4, one or more of the reflections 70, 75 and 80 of the transmitted microwave signal 50 are processed by the processing circuitry 12 to determine one or more characteristics of the waste water 85 flowing through the conduit 90. Determining one or more characteristics of the waste water 85 may include one or more of the following: quantifying the waste water flow through the conduit 90, determining which impurities are present in the waste water 85, and determining the quantity of a particular impurity that is present in the waste water 85.

Quantifying the waste water flow through the conduit 90 may involve determining the amount of waste water that is present in the conduit 90 at a particular instance in time, and/or determining the amount of waste water 85 that has flowed (or is flowing) through the conduit 90 over a period of time.

In order to determine the amount of waste water 85 contained in the conduit 90 at a particular time. For example, the processing circuitry 12 may determine the distance between the transceiver circuitry 14 and the surface 82 of the waste water 85. The processing circuitry 12 may determine this distance by processing at least one property of the first reflection 70 of the transmitted microwave signal 50. In this example, the at least one property is the time that elapsed between the transmission of the microwave signal 50 and the reception of the first reflection 70 of the microwave signal 50 $(t_2-t_1)$. Alternatively, the at least one property may be the amplitude of the first reflection 70, relative to the amplitude of the transmitted microwave signal 50.

If the distance d between the transceiver circuitry 14 and the surface 82 of the waste water 85 is known, and the dimensions of the conduit 90 and the waveguide 11 are known, the height h of the waste water 85 can be found.

If the dimensions of the conduit 90 are not known, the diameter of the conduit 90 can be estimated by determining the time that elapsed between the transmission of the microwave signal 50 and the reception of the third reflection 80 $(t_5-t_1)$.

Once the height h of the waste water 85 is known and the dimensions of the conduit 90 are also known, the hydraulic radius $R_h$ can be calculated using the following equation:

$$R_h = \frac{A}{P}$$

where: A=the cross sectional area of flow of the waste water 85 and P=the wetted perimeter of the conduit 90.

The cross sectional area of flow A indicates the amount of waste water 85 flowing through the conduit 90 at a particular time.

The average cross-sectional velocity or flow of the waste water 85 in the conduit 90 can be calculated using the Manning equation (also known as the Gauckler-Manning equation and the Gauckler-Manning-Strickler equation):

$$V = \frac{k}{n} R_h^{2/3} S^{1/2}$$

where: V=average cross-sectional velocity of the waste water 85, k=a conversion constant equal to 1 for SI units, n is the Gauckler-Manning co-efficient, $R_h$ is the hydraulic radius and S is the slope of the waste water surface.

The Gauckler-Manning co-efficient depends upon the material that the conduit 90 is made from. The slope of the waste water surface may be estimated to be the same as the slope of the conduit 90, which can be measured readily. Alternatively, the slope of the conduit 90 can be estimated by timing two different amounts of water travelling through the conduit 90, and solving the relevant simultaneous equation.

When the average cross sectional velocity V has been calculated, it can be used to determine the amount of waste water (for example, the volume of waste water) that has flowed through the conduit 90 over a period of time.

In some embodiments of the invention, the transceiver circuitry 14 may be configured to transmit microwave signals 50 periodically. In these embodiments of the invention, the first reflection 70 of each microwave signal 50 may be used to estimate the quantity of waste water (for example, the volume of waste water) that is flowing or that has flowed through the conduit 90 over a period of time.

The waste water assessment apparatus 10 may be calibrated to ensure that reliable results are being provided. The apparatus 10 may, for example, be calibrated by sending a known amount of water through the conduit 90 and comparing the known amount with the amount estimated by the processing circuitry 12.

The processing circuitry 12 may be configured to determine the nature of the flow of waste water 85 through the conduit. For example, the processing circuitry 12 may be configured to determine whether the flow of the waste water 85 is steady or turbulent. A steady flow of waste water 85 may, for example, have a reasonably constant height h within the conduit 90. A turbulent flow of waste water 85 may have a highly variable height h.

The Manning formula described above is particularly applicable to circumstances in which the waste water 85 has a steady flow. It will be appreciated by those skilled in the art that other techniques may be used to determine the average cross sectional velocity V of the waste water 85 if the flow is considered to be turbulent.

If the processing circuitry 12 determines that the height h of the waste water 85 has been constant for longer than a threshold period of time (for example, a number of hours or longer), it may determine that the conduit 90 is at least partially blocked. The waste water assessment apparatus 10 may have an alerting device (for example, a light source such as a light emitting diode and/or an audible alarm) that alerts a user to the presence of such a blockage.

The processing circuitry 12 may also be configured to determine whether one or more impurities are present in the water. As mentioned above, when the microwave signal 50 travels through the waste water 85, it is reflected by the impurities contained within the waste water 85. The second reflection 75 of the transmitted microwave signal 50 has one or more properties that indicate that one or more impurities are present in the waste water 85.

The processing circuitry 12 may be configured to process the second reflected signal 75 to determine whether it has one or more properties that are characteristic of the presence of a particular impurity or impurities. For example, the processing circuitry 12 may process the second reflected signal 75 to determine whether it has an amplitude, phase, frequency, polarization and/or degree of scattering that indicates that a particular material is present in the waste water 85, and to determine the quantity of that material that is present in the waste water 85. The processing circuitry 12 may be configured to perform an Inverse Fast Fourier Transform (IFFT) on the second reflected signal 75 in order to analyse it in the frequency domain. Tomographic techniques may be used to analyse the second reflected signal 75.

The second reflected signal 75 may be processed by the processing circuitry 12 in conjunction with the reference data 23 stored in the memory circuitry 19. For example, the reference data 23 may be a look-up table that comprises data identifying the reflected signal properties (such as amplitude, phase, frequency, polarization and/or degree of scattering) that are associated with the presence of a particular impurity in the waste water. For instance, the reference data 23 may include such reflected signal properties for a number of impurities.

When a set of properties from a particular second reflected signal 75 have been determined, the processing circuitry 12 may compare them with the properties stored in the reference data 23 to determine whether a particular impurity is present in the waste water 85 (such as hydrocarbons or metals) and also to determine how much of that impurity that is present in the waste water 85.

In summary, embodiments of the invention enable the quantity of waste water 85 being drained from a particular property to be accurately estimated. This may advantageously enable water companies to levy more accurate charges to customers.

Embodiments of the invention also enable the quality of waste water 85 being drained from a particular property to be accurately estimated. For example, embodiments of the invention may be used to estimate which impurities are present in the waste water and the quantities that are present. This potentially provides water companies and/or government bodies with an opportunity to levy a waste water charge that is proportionate with the level of pollution that is being caused by the owners/tenants of a particular property. It also enables illegal discharge (such as hydrocarbons and metals) to be identified.

References to 'computer-readable storage medium', 'computer program product', 'tangibly embodied computer program' etc. or a 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other devices. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

The blocks illustrated in FIG. 4 may represent steps in a method and/or sections of code in the computer program 20. The illustration of a particular order to the blocks does not necessarily imply that there is a required or preferred order for the blocks and the order and arrangement of the block may be varied. Furthermore, it may be possible for some steps to be omitted.

Although embodiments of the present invention have been described in the preceding paragraphs with reference to various examples, it should be appreciated that modifications to the examples given can be made without departing from the scope of the invention as claimed. For example, in the exemplary embodiments of the invention described above, the conduit 90 is described as being made from clay or a plastics material. In practice, the conduit 90 may be made from metal. If so, an aperture may be created in the conduit 90 to prevent transmitted microwaves from being reflected from the outside of the conduit 90.

UWB signals are considered to be particularly suitable for use in embodiments of the invention because they provide a fine spatial resolution, enable relatively easy extraction of target features from a reflected signal, are difficult to reproduce to the required degree of accuracy for the purpose of cheating the apparatus 10 and are unlikely to cause interference to nearby electronics. However, it will be appreciated by those skilled in the art that other forms of signal could be used.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. An apparatus, comprising:
   transceiver circuitry for periodically transmitting microwave signals through a wall of a closed conduit channeling waste water away from property and for receiving reflections of the microwave signals, from within the closed conduit, that have passed through the wall of the closed conduit;
   processing circuitry configured to:
      process one or more of the reflections of the microwave signals to determine a distance between the transceiver circuitry and a surface of the waste water flowing in the closed conduit;
      determine that the determined distance has been constant for a period of time;
      distinguish between a constant determined distance corresponding with a steady flow of waste water in the closed conduit and a constant determined distance corresponding with a blockage in the closed conduit by determining that there is the blockage in the closed conduit if the period of time is longer than a threshold period of time; and
      cause a user to be alerted as to a presence of the blockage in response to the processing circuitry determining that the determined distance between the transceiver circuitry and the surface of the waste water has been constant for the period of time longer than the threshold period of time.

2. The apparatus as claimed in claim 1, wherein a height of the waste water in the closed conduit is determined using the determined distance between the transceiver circuitry and the surface of the waste water.

3. The apparatus as claimed in claim 1, wherein an alert is provided by at least one of a light emitting diode or an audible alarm.

4. The apparatus as claimed in claim 1, further comprising a housing, wherein the processing circuitry is located in the housing.

5. The apparatus as claimed in claim 4, wherein an alert is provided by an alerting device that is located outside the housing.

6. The apparatus as claimed in claim 1, wherein the processing circuitry is configured to quantify waste water flow through the closed conduit using the determined distance.

7. The apparatus as claimed in claim 1, wherein the processing circuitry is configured to determine an amount of waste water flowing through the closed conduit at a particular time by processing at least one property of a first reflection of a transmitted microwave signal.

8. The apparatus as claimed in claim 7, wherein the at least one property includes a first amplitude of the first reflection of the transmitted microwave signal relative to a second amplitude of the transmitted microwave signal.

9. The apparatus as claimed in claim 7, wherein the at least one property includes a time elapsed between the transmission of the microwave signal and a reception of the first reflection of the transmitted microwave signal.

10. The apparatus as claimed in claim 1, wherein the processing circuitry is configured to determine an amount of waste water that has flowed through the closed conduit over a period of time by processing at least one property of a first reflection of a transmitted microwave signal.

11. The apparatus as claimed in claim 1, wherein the processing circuitry is configured to process one or more of the reflections of the microwave signals to determine whether one or more impurities are present in the waste water.

12. The apparatus as claimed in claim 11, wherein the one or more impurities comprise one or more hydrocarbons and/or one or more metals.

13. The apparatus as claimed in claim 11, wherein the processing circuitry is configured to determine whether one or more impurities are present in the waste water by determining at least one of: an amplitude, phase, frequency, polarization and degree of scattering of one or more reflections of the microwave signals.

14. The apparatus as claimed in claim 11, wherein the processing circuitry is configured to process one or more reflections of the microwave signals to determine a quantity of a particular impurity present in the waste water.

15. The apparatus as claimed in claim 1, wherein the transmitted microwave signals are ultra wide band microwave signals.

16. The apparatus as claimed in claim 1, further comprising a waveguide configured to guide transmitted microwave signals through the wall of the closed conduit.

17. A method, comprising:
   periodically transmitting microwave signals, using transceiver circuitry, through a wall of a closed conduit channeling waste water away from property;
   receiving, at the transceiver circuitry, reflections of the microwave signals, from within the closed conduit, that have passed through the wall of the closed conduit;
   processing one or more of the reflections of the microwave signals to determine a distance between the transceiver circuitry and a surface of the waste water flowing in the closed conduit;
   determining that the determined distance has been constant for a period of time;
   distinguishing between a constant determined distance corresponding with a steady flow of waste water in the closed conduit and a constant determined distance corresponding with a blockage in the closed conduit by determining that there is the blockage in the closed conduit if the period of time is longer than a threshold period of time; and causing a user to be alerted as to a presence of the blockage in response to a determination that the determined distance between the transceiver circuitry and the surface of the waste water has been constant for the period of time longer than the threshold period of time.

18. The method as claimed in claim 17, further comprising: fitting transceiver circuitry, for periodically transmitting the microwave signals, to a position adjacent to the closed conduit and outside the closed conduit.

19. A non-transitory computer-readable medium storing a computer program comprising computer program instructions that, when executed by processing circuitry, cause the method as claimed in claim 17 to be performed.

20. An apparatus, comprising:

transceiver means for periodically transmitting microwave signals through a wall of a closed conduit channeling waste water away from property and for receiving reflections of the microwave signals, from within the closed conduit, that have passed through the wall of the closed conduit;

means for processing one or more of the reflections of the microwave signals to determine a distance between the transceiver means and a surface of the waste water flowing in the closed conduit;

means for determining that the determined distance has been constant for a period of time;

means for distinguishing between a constant determined distance corresponding with a steady flow of waste water in the closed conduit and a constant determined distance corresponding with a blockage in the closed conduit by determining that there is the blockage in the closed conduit if the period of time is longer than a threshold period of time; and means for causing a user to be alerted as to a presence of the blockage in response to a determination that the determined distance between the transceiver means and the surface of the waste water has been constant for the period of time longer than the threshold period of time.

* * * * *